United States Patent [19]
Lessing, Jr.

[11] Patent Number: 5,688,248
[45] Date of Patent: Nov. 18, 1997

[54] ADULT AND PEDIATRIC PERITONEAL DIALYSIS CATHETER BELT PACK

[76] Inventor: Kenneth C. Lessing, Jr., 1344 Laverte Cir., Mableton, Ga. 30059

[21] Appl. No.: 641,826

[22] Filed: May 2, 1996

[51] Int. Cl.⁶ .................................................. A61M 25/02
[52] U.S. Cl. ................... 604/179; 604/174; 128/DIG. 26
[58] Field of Search ........................... 604/179, 174, 604/175, 176, 177, 178, 180; 128/DIG. 26

[56] References Cited

U.S. PATENT DOCUMENTS

| | | | |
|---|---|---|---|
| 3,946,742 | 3/1976 | Eross | 128/DIG. 26 X |
| 4,596,560 | 6/1986 | Simpsons | 128/DIG. 26 X |
| 4,666,434 | 5/1987 | Kaufman | 604/179 |
| 5,425,719 | 6/1995 | Lessing, Jr. | 604/179 |
| 5,437,273 | 8/1995 | Bates et al. | 128/DIG. 26 X |
| 5,468,229 | 11/1995 | Chandler | 128/DIG. 26 X |
| 5,496,282 | 3/1996 | Militzer et al. | 604/179 |

Primary Examiner—Sam Rimell
Assistant Examiner—Luke J. Yeh
Attorney, Agent, or Firm—Hinkle & Associates, P.C.

[57] ABSTRACT

A belt-pack for containing and securing surgically implanted catheters embodying a pouch, and a belt with two end portions, one end portion permanently attached to the pouch and one end portion thereof extending around the waist of a patient and overlapping and detachably connected to the pouch. The detachable connection of the one end belt portion and the pouch comprises multiple button holes in the belt portion for connecting to matching buttons affixed to the pouch to give a substantial range of adjustment for both adult and pediatric patients.

2 Claims, 2 Drawing Sheets

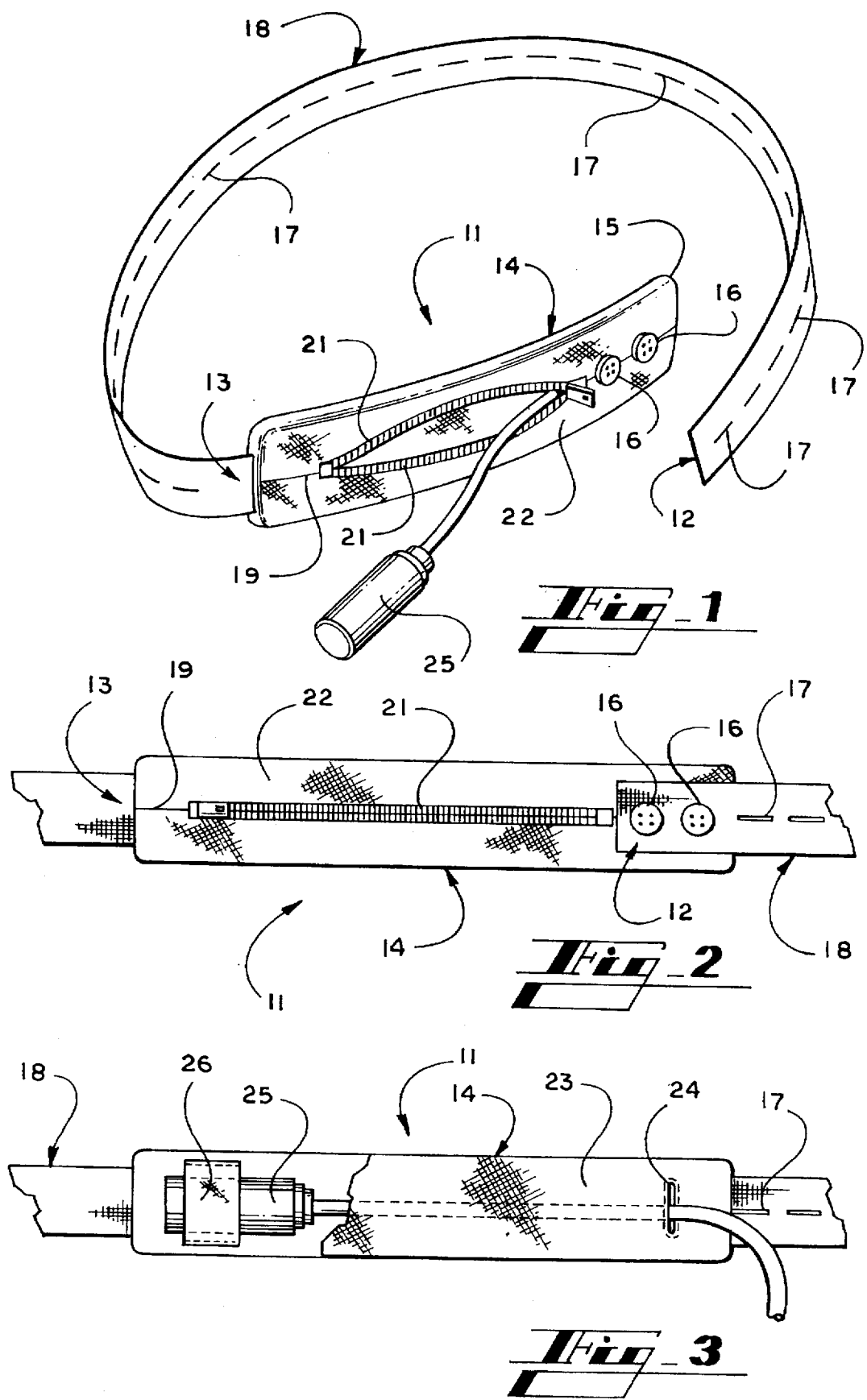

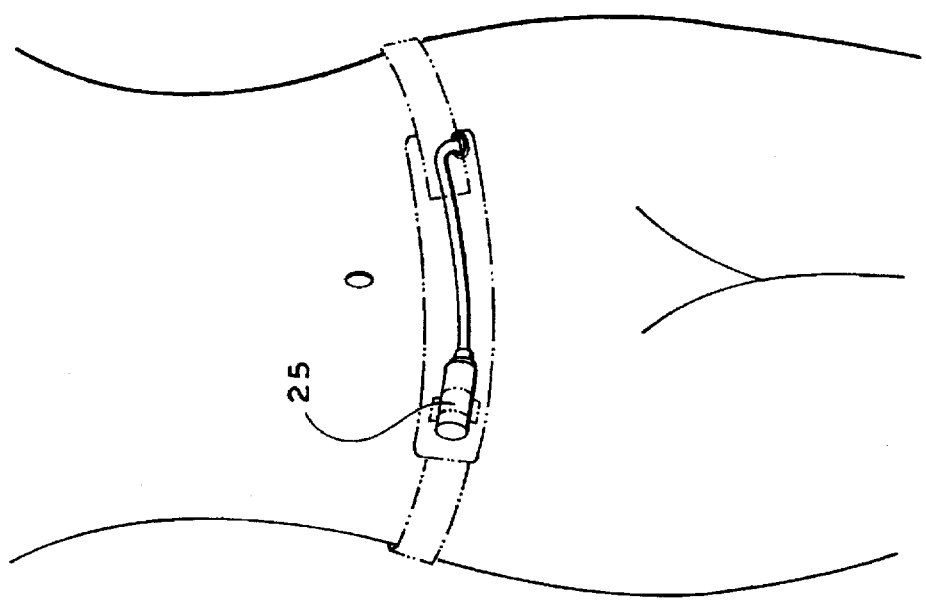
Fig_4B
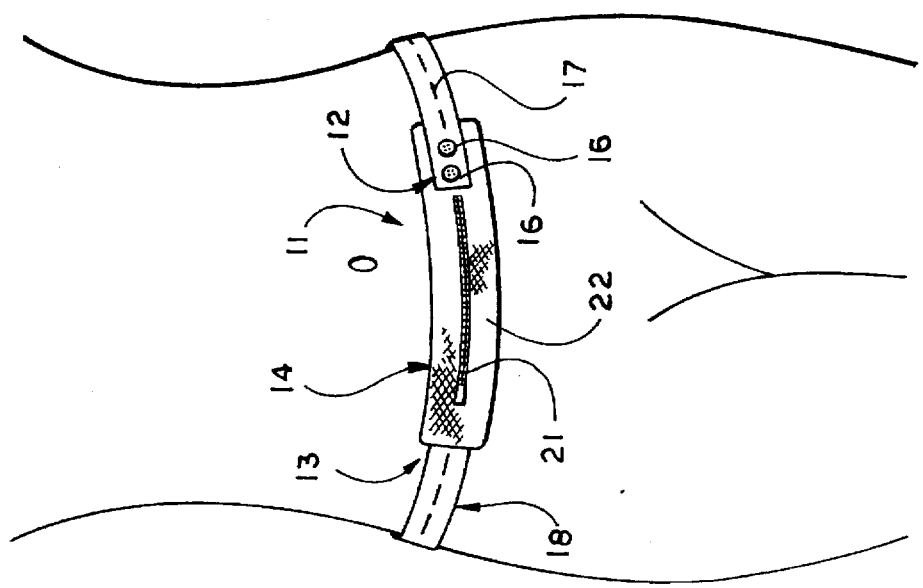
Fig_4A

ADULT AND PEDIATRIC PERITONEAL DIALYSIS CATHETER BELT PACK

BACKGROUND OF THE INVENTION

I. Field of the Invention

This invention relates in general to a belt pack for containing and securing surgically-implanted catheters. More specifically, the present invention relates to catheters which have been surgically implanted for the purpose of continuous ambulatory and continuous cycling peritoneal dialysis, and which are contained in a belt pack adjustable for both children and adults.

II. Description of the Related Art.

More than 80,000 Americans have chronic kidney failure and have to find other ways of doing the job their kidneys can no longer perform. Two such ways are continuous ambulatory and continuous cycling peritoneal dialysis which use the lining of the abdomen as a natural filter to remove water and wastes from the blood by putting a sterile cleansing solution, called dialysate, into the abdominal cavity and then draining this fluid after it has absorbed water wastes. There are two ways to fill and drain the peritoneal cavity:

(1) manually, by continuous ambulatory peritoneal dialysis, 4–6 times every day, or (2) automatically, by continuous cycling peritoneal dialysis, overnight while the patient sleeps.

Both procedures require the surgical implantation of a catheter apparatus which creates the problem of containing and securing the catheter apparatus when not being used in either treatment procedure. Current containment devices consist of securing the catheter apparatus by merely taping a section of the catheter apparatus directly to the patient's body. This taping method is unsatisfactory because:

(1) Frequent removal of the tape, as in the continuous ambulatory peritoneal dialysis treatment method, 4-6 times daily, can result in physical discomfort.

(2) The tape is not re-usable.

(3) The tape secures only a portion of the catheter apparatus, leaving the majority of the apparatus exposed.

(4) The taping method is aesthetically undesirable because it inhibits the pursuit of a normal, active lifestyle, including physical intimacy.

My previous patent (U.S. Pat. No. 5,425,719) disclosed a catheter belt pack similar to the present invention, but it lacked a significant aspect of this invention. Namely, my prior patent lacked the ability to be significantly adjustable for both adult and pediatric patients. The present invention overcomes that shortcoming.

SUMMARY OF THE INVENTION

The principle object of the present invention is to provide a more convenient, comfortable and desirable device for use securing surgically-implanted peritoneal dialysis catheters by containment in a durable, re-usable belt pack. More particularly, the invention provides a belt having buttons for effecting substantial adjustment of the belt around the wearer. Previous belts of this type were not effective for use with both adults and infants because the adjustment mechanism would not adjust from a large waist to a very small waist. This invention solves such problems by having a plurality of button holes in the belt throughout its length which cooperate with a button fastening system on the pouch to permit a wide range of adjustment of the belt.

Other objects, advantages and capabilities of the invention will become apparent from the following description taken in conjunction with the accompanying drawings showing preferred embodiments of the invention.

BRIEF DESCRIPTION OF THE DRAWINGS

FIG. 1 is a perspective view of my peritoneal dialysis catheter belt pack and the majority of component parts;

FIG. 2 is a front elevational view of the pouch-like member with portions of the belt broken away;

FIG. 3 is a rear elevation view of the pouch-like member, partially in section showing the catheter and the securing means for the catheter;

FIG. 4A is a front elevation view of the invention as it would be worn by the user; and FIG. 4B is a front elevation view of a user showing a surgically-implanted catheter apparatus with the peritoneal dialysis catheter belt pack shown in broken lines.

DESCRIPTION OF THE PREFERRED EMBODIMENTS

Referring to the drawings, wherein like reference characters show corresponding parts throughout the several figures, the belt-like catheter pack 11 is preferably of flexible woven material with two end portions 12 and 13 joined to pouch-like member 14 preferably of stable, woven material. End portion 12 is releasably fastened to the pouch 14. The catheter pack 11 is of a length to extend around the waist of a patient, whether adult or child, having a surgically-implanted catheter apparatus and will overlap an adjacent portion of the pouch 14 as shown in FIG. 1 and in FIG. 2.

The releasable end portion 12 of the catheter pack 11, and the fastening end 15 of the pouch 14 have cooperating surfaces facing each other, with the fastening end 15 carrying a plurality of buttons 16 in position to engage corresponding button holes 17 carried by the entire length of belt 18. The belt 18 is preferably of elasticized material to enhance the adjustability of the belt. The pouch 14 preferably comprises a single piece of woven material. The single piece of material would be so folded so that the free edges of the fold would meet at fold line 19 wherein a zipper 21 would be placed to gain access to the interior of the pouch 14 through an opening of a size sufficient to enclose and contain the catheter apparatus. FIGS. 1 and 2 show the reclosable zipper opening 21 running lengthwise across the center face 22 of the pouch 14, and along fold line 19 to facilitate access to the catheter apparatus. The back face 23 of pouch 14 contains a vertical, buttonhole-like slit 24 on one end through which the catheter apparatus 25 is inserted with a beltloop-like member 26 preferably of flexible, woven material attached to the inside-facing opposite end to secure the catheter apparatus 25. The belt-like loop member 26 might also be an elastic band to secure the catheter apparatus to the pouch.

In actual use, a patient with a catheter apparatus 24 surgically installed, will encircle the waist with the catheter pack 11 and will insert the catheter apparatus 24 through the buttonhole-like slit 24 in the back face 23 of the pouch 14 and secure the catheter 25 by placing its end through the beltloop-like member 26 which is accessed through the reclosable opening 21 in the front face 22 of the pouch 14. With the reclosable opening 21 remaining open, the patient wraps the belt 18 around his waist in position for any pair of button holes 17 to overlay and engage juxtaposed buttons 16. Next, the patient adjusts the catheter apparatus 25 within the pouch 14 and closes the reclosable opening 21. The patient is now ready to pursue his regular activities with the catheter apparatus fully contained and securely held in place as shown in FIG. 4B.

The belt 18 is made of conventional belt-type material such as non-roll waistband elastic, nylon webbing or other synthetic or natural flexible woven materials. However, to be fully functioning it is anticipated that the belt should be made of elastic material so that it will fit snugly about the patient. The pouch 14 is made of conventional stable woven materials such as cotton, polyester, cotton-polyester blends or other synthetic or natural stable woven materials. Furthermore, the materials might be conventional lingerie and undergarment materials so that the peritoneal dialysis catheter belt pack also functions as a conventional undergarment.

Various modifications may be made of the invention without departing from the scope thereof and it is desired, therefore, that only such limitations shall be placed thereon as are imposed by the prior art and which are set forth in the appended claims.

What is claimed is:

1. A peritoneal dialysis catheter apparatus containment device comprising:

a belt having a first end and a second end, the first end comprising an integral pouch, the pouch having a front face, a back face, front opening and a back opening, the front face and the back face defining a cavity within the pouch, a first releasable attaching means attached to the front face, the front opening having a zipper for selectively opening and closing the pouch, a second releasable attaching means for releasably attaching the second end to the first and, the first releasable attaching means being at least one button and the second releasably attaching means being at least one button hole located in the belt, the pouch being elongated in length and having a defined fold line along the length, the zipper being disposed along the fold line.

2. The peritoneal dialysis catheter apparatus containment device as claimed in claim 1, wherein the first releasable attaching means is located along the fold line.

* * * * *